(12) United States Patent
Oguma

(10) Patent No.: US 6,370,425 B1
(45) Date of Patent: Apr. 9, 2002

(54) BODY FAT METER AND WEIGHING INSTRUMENT WITH BODY FAT METER

(75) Inventor: Koji Oguma, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/551,397

(22) Filed: Apr. 17, 2000

Related U.S. Application Data

(63) Continuation of application No. PCT/JP98/04547, filed on Oct. 8, 1998.

(30) Foreign Application Priority Data

Oct. 17, 1997 (JP) .............................. 9-299603

(51) Int. Cl.[7] .............................. A61B 5/05
(52) U.S. Cl. .................................... 600/547
(58) Field of Search ............................ 600/547, 372, 600/548; 128/639, 734, 696

(56) References Cited

U.S. PATENT DOCUMENTS

| | | | |
|---|---|---|---|
| 4,008,712 A | | 2/1977 | Nyboer |
| 4,947,862 A | * | 8/1990 | Kelly .................... 600/547 |
| 4,949,727 A | * | 8/1990 | Yamazaki et al. ........... 600/547 |
| 5,335,667 A | * | 8/1994 | Cha et al. ................ 600/547 |
| 5,372,141 A | * | 12/1994 | Gallup et al. .............. 600/547 |
| 5,415,176 A | * | 5/1995 | Sato et al. ................ 600/547 |
| 5,579,782 A | * | 12/1996 | Masuo ..................... 600/547 |
| 5,611,351 A | * | 3/1997 | Sato et al. ................ 600/547 |
| 5,720,296 A | * | 2/1998 | Cha ....................... 600/547 |
| 5,817,031 A | * | 10/1998 | Masuo et al. .............. 600/547 |

FOREIGN PATENT DOCUMENTS

| | | |
|---|---|---|
| JP | 53-20368 | 2/1978 |
| JP | 57-154069 | 9/1982 |
| JP | 59-82862 | 6/1984 |
| JP | 1-287473 | 11/1989 |
| JP | 2-279135 | 11/1990 |
| JP | 5-49050 | 7/1993 |
| JP | 7-12635 | 1/1995 |
| JP | 7-51242 | 2/1995 |

OTHER PUBLICATIONS

"Assessment of Fat–Free Mass Using Bioelectrical Impedance Measurements of the Human Body", by Lukaski et al., The American Journal of Clinical Nutrition, vol. 41, Apr. 1985, pp. 810–817.

* cited by examiner

Primary Examiner—Kevin Shaver
Assistant Examiner—Brian Szmal
(74) Attorney, Agent, or Firm—McDermott, Will & Emery

(57) ABSTRACT

There is provided a weighing instrument with body fat meter which can compensate for variation in contact impedance between a human body and a measuring electrode due to wearing socks or the like. The weighing instrument comprises a constant-voltage power source as a current power source for measuring a bioelectrical impedance and a current measuring device installed between the constant-voltage power source and a voltage supply terminal to measure an internal influent current and determine an internal impedance on the basis of the measured internal influent current and a potential difference between voltage measurement terminals.

6 Claims, 7 Drawing Sheets

BODY FAT METER AND WEIGHING INSTRUMENT WITH BODY FAT METER

REFERENCE TO RELATED APPLICATION

This Application is a continuation of International Application No. PCT/JP98/04547, whose international filing date is Oct. 8, 1998, which in turn claims the benefit of Japanese Application No. 299603/1997, filed Oct. 17, 1997, the disclosures of which Applications are incorporated by reference herein. The benefit of the filing and priority dates of the International and Japanese Applications is respectfully requested.

TECHNICAL FIELD

The present invention relates to a weighing instrument with body fat meter for measuring simultaneously a bioelectrical impedance between both feet of a person in standing position and a weight, and for calculating and estimating a body fat amount based on such physical features as a height, a sex, an age and the like which are inputted other than above measurements, and, in particular, relates to a weighing instrument with body fat meter which responds to variations in a contact impedance between an electrode for measuring impedance and a sole of foot as a measured body.

BACKGROUND ART

Body fat meter which utilizes the fact that the composition of a human body can be estimated by the use of an impedance between ends of human body which can be obtained by applying a feeble constant current to an end of a measured person's body and measuring a voltage drop between electrodes (The American Journal of Clinical Nutrition, 41(4) 810–817 1985 "Assessment of fat-free mass using bioelectrical impedance measurement of the human body") was proposed (by U.S. Pat. No. 4,008,721, JP 5-49050C, JP 7-51242A, etc.) and the products based on these proposals have been introduced into market. Among them, the product according to JP 5-49050C is introduced into market as an instrument which allows to estimate body fat with absolute ease, that is, a weighing instrument with body fat meter, wherein a flat metal electrode for measuring a bioelectrical impedance is attached to a position on a top surface of a loading board of a weighing instrument with which soles of both feet of a measured person come in contact when he gets on the weighing instrument, whereby, among factors for estimating the body fat amount, an impedance between ends of human body and a weight which vary in every measurement can be measured simultaneously and can be taken into calculation formulas.

In a conventional body fat meter, at first, such physical data as a height, a sex, a weight and the like are inputted through such an input device as a key switch and the like and are stored in a memory, and then an impedance measuring device is driven by a controller to output a bioelectrical impedance in an analogue form, and then said analogue impedance is converted into digital value by an A/D converter to be taken into an arithmetic processor, which calculates a body fat amount from the digital value of the bioelectrical impedance and the physical data such as the height and the like stored in the memory, and outputs to an indicator. Since a weight, different from other physical data, changes easily, and thereby it should be inputted every time for a measurement, a weighing instrument is installed so as for a weight of a measured person to be measured every time when an impedance is measured in the weighing instrument with the body fat meter.

This weighing instrument with the body fat meter has an alternation switch between an analogue output of the impedance measuring device and said A/D converter, and another end of the alternation switch is connected to an analogue output of the weighing instrument, and a control terminal of the alternation switch is connected to said controller, wherein, at first, an output of the weighing instrument is inputted into the A/D converter through the alternation switch to convert a weight value of a measured person into a digital value and to store said digital value in a memory, and then the alternation switch is switched to input an output of the impedance measuring device into the A/D converter to convert a measured value of the impedance into a digital value, so that the A/D converter is shared by the weighing instrument and the impedance measuring device (FIG. 1).

In addition, the bioelectrical impedance measuring device of said conventional weighing instrument with body fat meter employs four-terminal method in order to eliminate an influence of variation in a contact resistance between an electrode and a human body upon a measured value (FIGS. 2 and 3).

Electrodes A1, A2, B1 and B2 are arranged so that said electrodes come to contact with tiptoes and heels of both feet of the measured person when he gets on the loading plate of an electronic weighing instrument for measuring the weight of the measured person, and current terminals of a constant-current regulated AC power source with known current value of iR in 50 kHz are connected to the electrodes A1 and A2 and measurement terminals of AC voltmeter are connected to the electrodes B1 and B2. This system is designed so that little current would flow into the measurement terminals of the AC voltmeter.

A bioelectrical impedance is represented by ri, a contact impedance of the right tiptoe by rA1, a contact impedance of the left tiptoe by rA2, a contact impedance of the right heel by rB1, and a contact impedance of the left heel is represented by rB2.

A constant-current regulated alternating current iR flows from rA1 through ri and rA2 and returns to the current terminal without being leaked to rB1 and rB2.

At that time, the voltage drops made by rA1, ri and rA2 are shown as below respectively.

$$vA1 = iR \times rA1 \quad (1)$$

$$vi = iR \times ri \quad (2)$$

$$vA2 = iR \times rA2 \quad (3)$$

Since little current flows into each measurement terminal of the AC voltmeter, voltage drops made by rB1 and rB2 could be counted to be zero, that is, the effects caused by rB1 and rB2 could be negligible, so that vi can be directly observed by the AC voltmeter.

From the equation (2), the internal impedance ri is calculated as:

$$ri = vi/iR \quad (4)$$

so that said impedance ri can be derived from the observed value vi because iR is a known value.

The constant-current regulated AC power source comprises a constant-voltage regulated AC power source, a resistor R1 and an OP amplifier (FIG. 4).

An output of the constant-voltage regulated AC power source is connected to an end of the resistor R1 and another end of the resistor R1 is connected to a negative terminal of the OP amplifier. To the negative terminal is connected said electrode A1, to an output terminal of the OP amplifier is connected said electrode A2, and a positive terminal of the OP amplifier is connected to GND (0V). The negative terminal of the OP amplifier has the same potential as the positive terminal does as far as the output terminal is not saturated, and no current flow in from the negative terminal into the OP amplifier. Accordingly, the current flowing into the resistor R1 directly flows into the electrode A1 through the human body, reaches to the electrode A2 and is absorbed by the output terminal of the OP amplifier. When the output voltage of the constant-voltage regulated AC power source is v, the voltage between both ends of the resistor R1 is v, so that:

$$ri=v/R1 \tag{5}$$

that is, the known constant-current can be obtained because v and R1 are known values.

The AC voltmeter comprises a differential amplifier, a rectifier, a low pass filter and an A/D converter. At first, the voltage between the electrodes B1 and B2 is amplified into N-times thereof by the differential amplifier.

At that time, an output voltage of the differential amplifier v is represented as below.

$$v=N \times Vi=N \times iR \times ri \tag{6}$$

When this output is inputted into the half-wave rectifier, the rectifier outputs only a positive portions of the AC voltage. This output is transformed into DC by the low pass filter and inputted into the A/D converter and then the digital values proportional to the internal impedance ri is obtained.

By these procedure, the bioelectrical impedance free from the contact impedance of the feet can be measured.

In order to perform a precise measurement as much as possible, however, this system is designed generally on the assumption that the contact impedance is small to some degree and the system is used with bare feet. The contact impedance of a sole is generally less than 1 k$\Omega$, so that the maximum current value for measuring the impedance is assumed to be less than 1 mA in the design specifications.

When the peak voltage of said constant-voltage regulated AC power source is 0.8 V and the resistor R1 is 1 k$\Omega$, the current value is derived to be 800 $\mu$A from the equation (5).

When the bioelectrical impedance is 500 $\Omega$, and each contact impedance is 1 k$\Omega$, the voltage V0 of the electrode A2 is calculated as below.

$$V0=800 \ \mu A \times (rA1+ri+rA2)=2 \ V$$

Generally, the contact impedance of the sole is less than 1 k$\Omega$, but, when the socks or stockings are put on the feet, it increases extremely.

If the contact impedance is assumed to be 10 k$\Omega$, the voltage V0 of the electrode A2 would be calculated as below.

$$V0=800 \ \mu A \times (10k\Omega+500\Omega+10k\Omega)=16.4 \ V \tag{8}$$

On the other hand, most body fat meter is designed to be portable and a circuit thereof is powered by a battery. Accordingly, a circuit voltage is limited to a degree of ±5 V. A voltage of the output terminal of the OP amplifier used in the constant-current regulated power source is within said range, so that, when the socks or stockings are put on the feet (that is, the contact impedance is 10 k$\Omega$) as described above, the OP amplifier is saturated and the constant current cannot be applied thereto. As a result, ri is not a known value of constant current, and a wave form thereof is deformed and goes out of sinusoidal wave form. However, the AC voltmeter would detect said deformed and incorrect voltage output vi, and, using said vi value, the arithmetic processor would calculate the body fat amount to output it to the indicator.

As having been described above, the bioelectrical impedance measuring device of the conventional weighing instrument with body fat meter is designed on the assumption that the measured person gets on the measuring instrument by the bare feet, and, accordingly, when the socks or stockings are put on the feet and thereby the contact impedance between the electrode of the measuring device and the measured body becomes too large, the voltage drop between the electrode of the measuring device and the measured body increases due to the constitution of the system and it goes out of a normal operation range of the constant-current power source, so that a predetermined degree of current cannot be applied to the human body and thereby an accurate measurement cannot be performed.

An object of the present invention is to provide a weighing instrument with body fat meter which allows a body fat to be precisely and simply measured even if a contact impedance between a human body and an electrode for measuring a bioelectrical impedance increases as a result of wearing socks and the like.

DISCLOSURE OF INVENTION

A constant-voltage power source is employed as a current power source for measuring a bioelectrical impedance, and a current measuring device is installed between said constant-voltage power source and an electrode of a voltage supply terminal to measure a current flowing into a human body (hereafter referred to as internal influent current), and then an impedance between both feet is determined based on a measured value of the internal influent current and a potential difference between voltage measurement terminals (FIG. 8).

The internal influent current -power source operates within the normal operating range without being affected by the contact impedance value, and the internal influent current and the potential difference between voltage measurement terminals which are used as base data for calculating the impedance are measured accurately, so that the bioelectrical impedance can be precisely measured even if there exists large contact impedance.

According to an aspect of the present invention, there are provided two pairs of electrodes of a measuring device for measuring a bioelectrical impedance between both feet, said two pairs of electrodes being composed of a pair of electrodes A (A1, A2) which comes in contact with the tiptoes of both feet when a measured person gets on a loading board of an electronic weighing instrument for measuring a weight thereof and makes a feeble current flow into the human body thereof and a pair of electrodes B (B1, B2) which comes in contact with the heels of both feet thereof and measures a potential difference between both heels, and an input device for inputting such physical features as a height, an age, a sex and the like. An output of a sinusoidal wave oscillator is lead to the electrode A via a resistor R1 with known resistance value, and the internal influent current is derived from the potential difference caused by the voltage drop by the resistor R1. On the other hand, the potential difference due to the voltage drop between the electrodes B is taken out by a differential amplifier, and the output thereof is, after a wave forming and a rectifying processing being applied thereto and being converted into the direct current, processed by the A/D conversion and then is taken into an arithmetic processing section as a digital data of the bioelectric impedance by the use of a current value derived from the potential difference between both ends of the resistor R1. The arithmetic processing section calculates a body fat amount based on the inputted physical features such as the height, the age, the sex and the like, a measured or inputted weight value and the bioelectrical impedance, and then the output is indicated on an indicator installed on a top surface of the loading board.

There will now be described in detail preferred embodiments of the present invention with reference to the drawings.

BEST MODE FOR CARRYING OUT THE INVENTION

Figure 1:
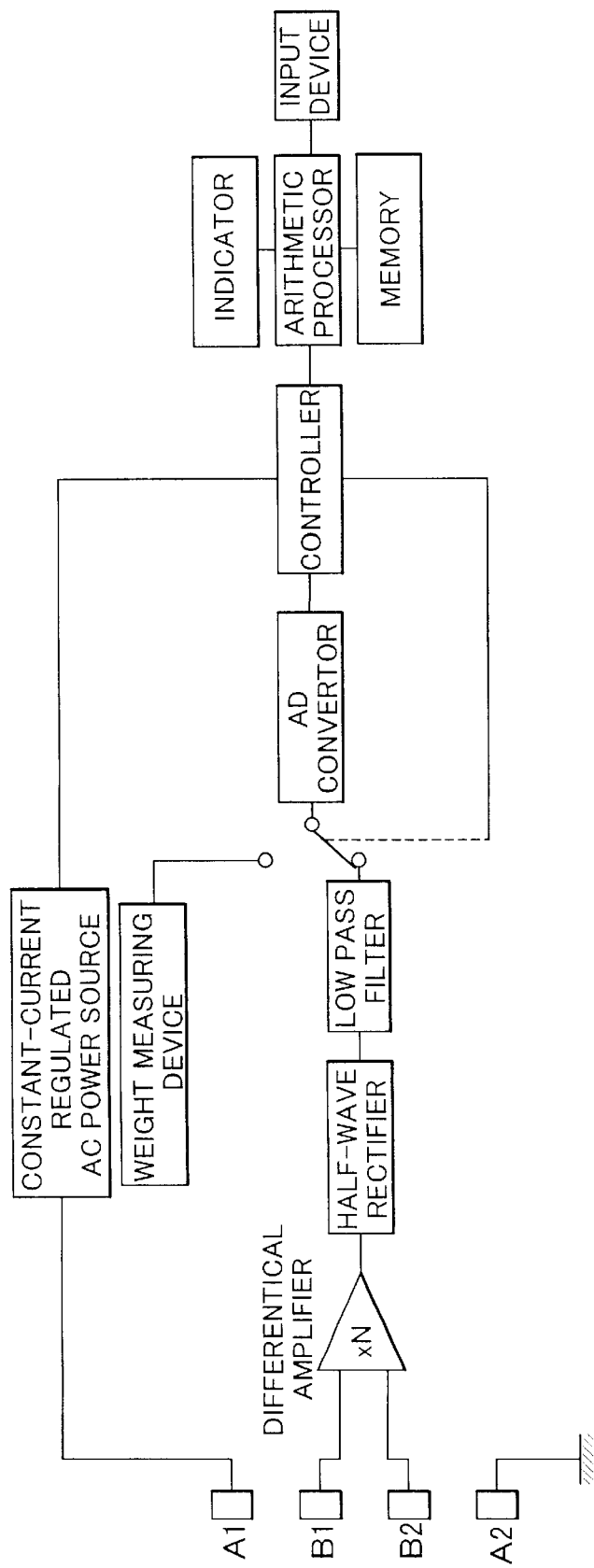
FIG. 1 is a block diagram of the conventional weighing instrument with the body fat meter.
Figure 2:
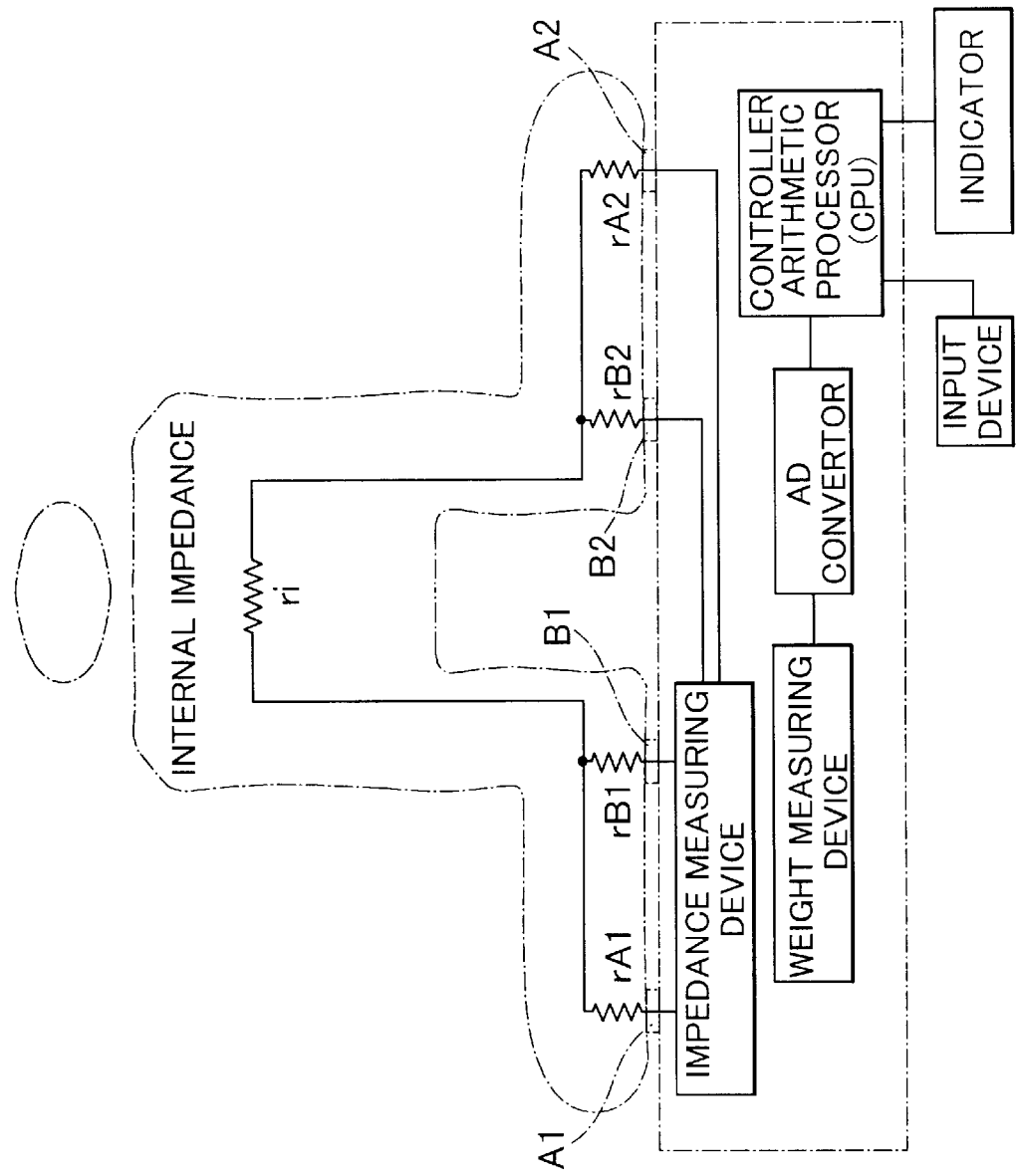
FIG. 2 is a typical drawing illustrating a measuring system of body fat.
Figure 3:
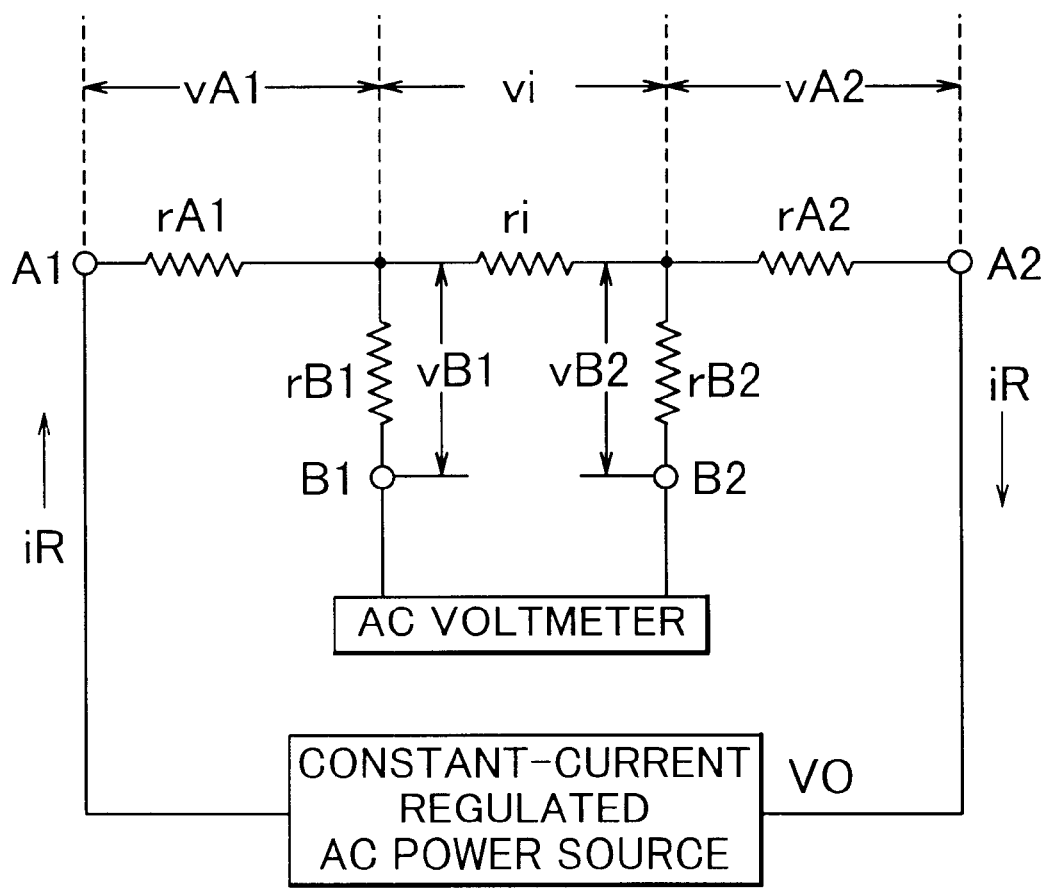
FIG. 3 is an explanatory drawing illustrating a measuring system of bioelectrical impedance.
Figure 4:
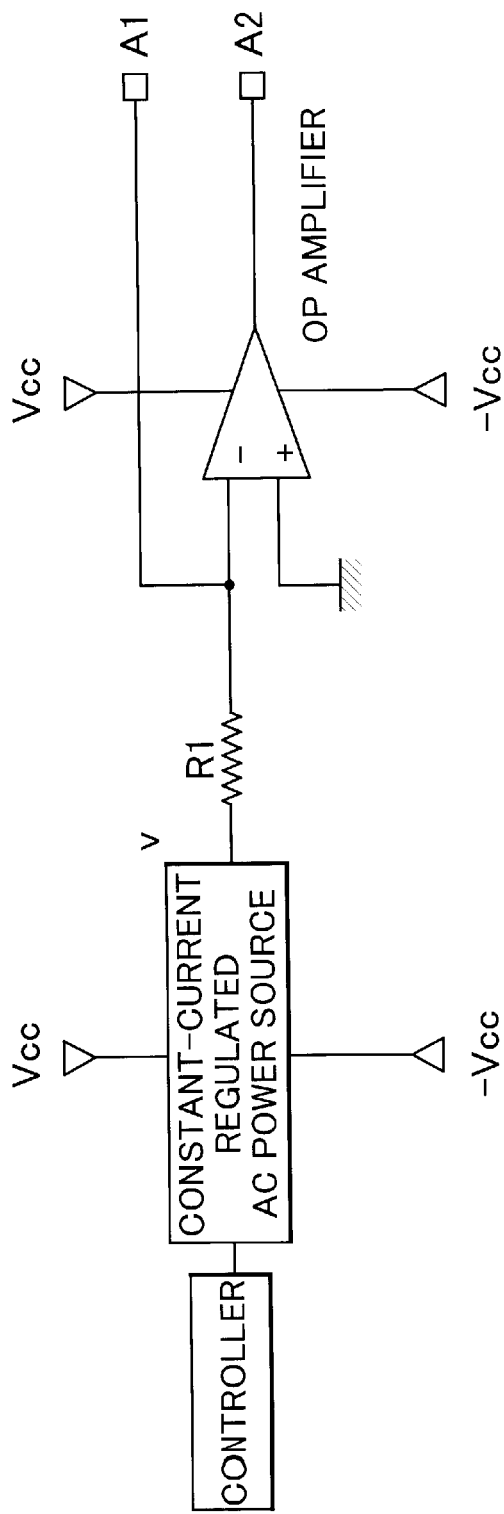
FIG. 4 is a block diagram illustrating a constant-current system.
Figure 5:
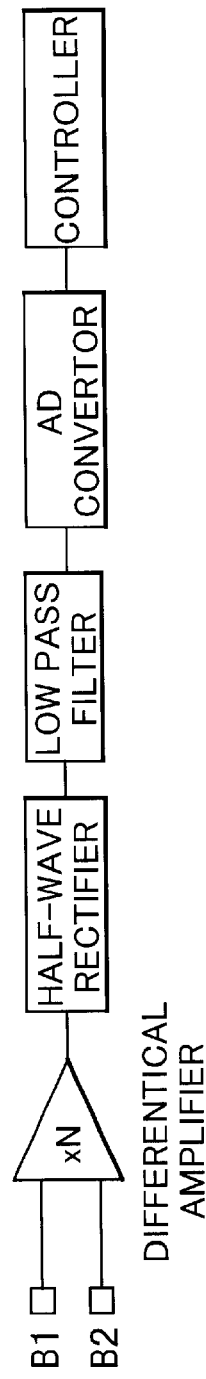
FIG. 5 is a block diagram illustrating an AC voltmeter.
Figure 6:
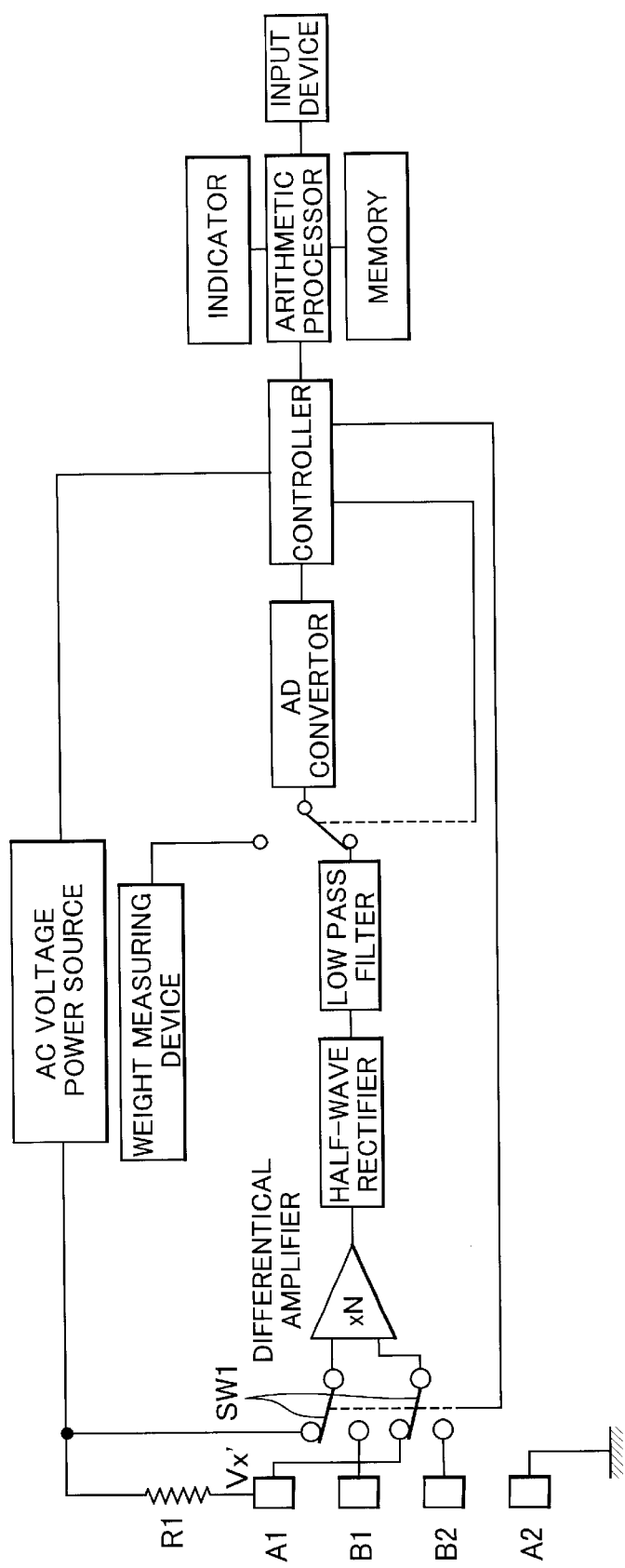
FIG. 6 is a black diagram of the embodiment of the present invention.
Figure 7:
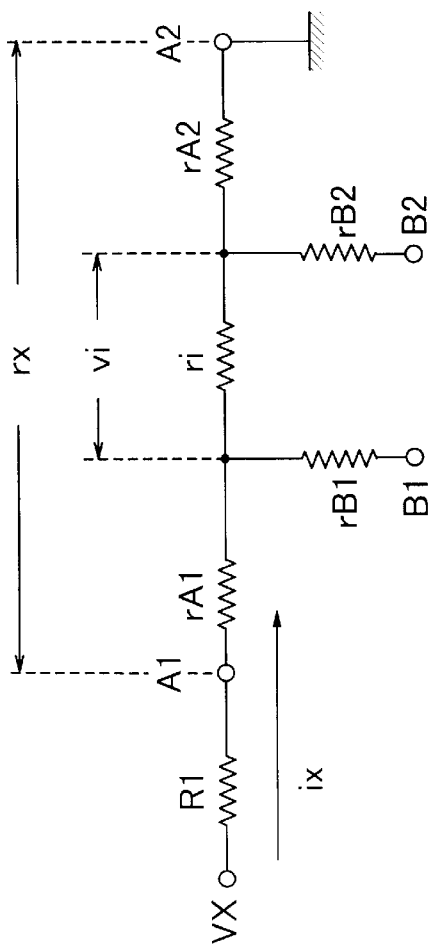
FIG. 7 is an explanatory drawing of the present invention.
Figure 8:
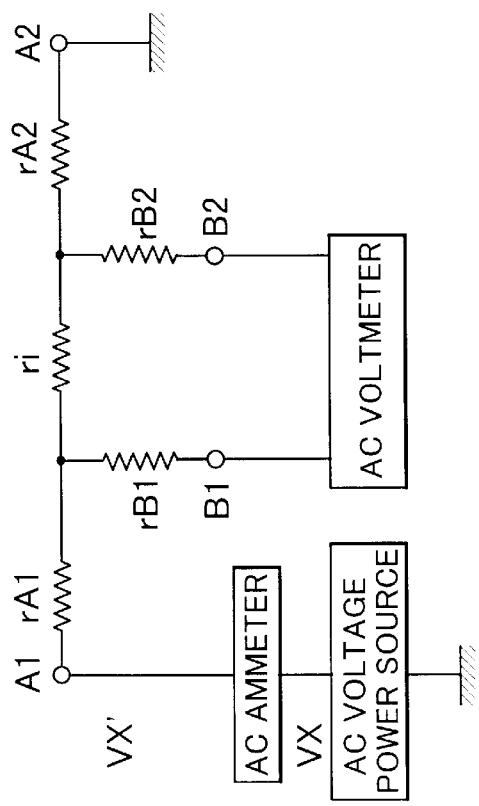
FIG. 8 is a block diagram illustrating a means to solve the problem according to the present invention.
Figure 9:
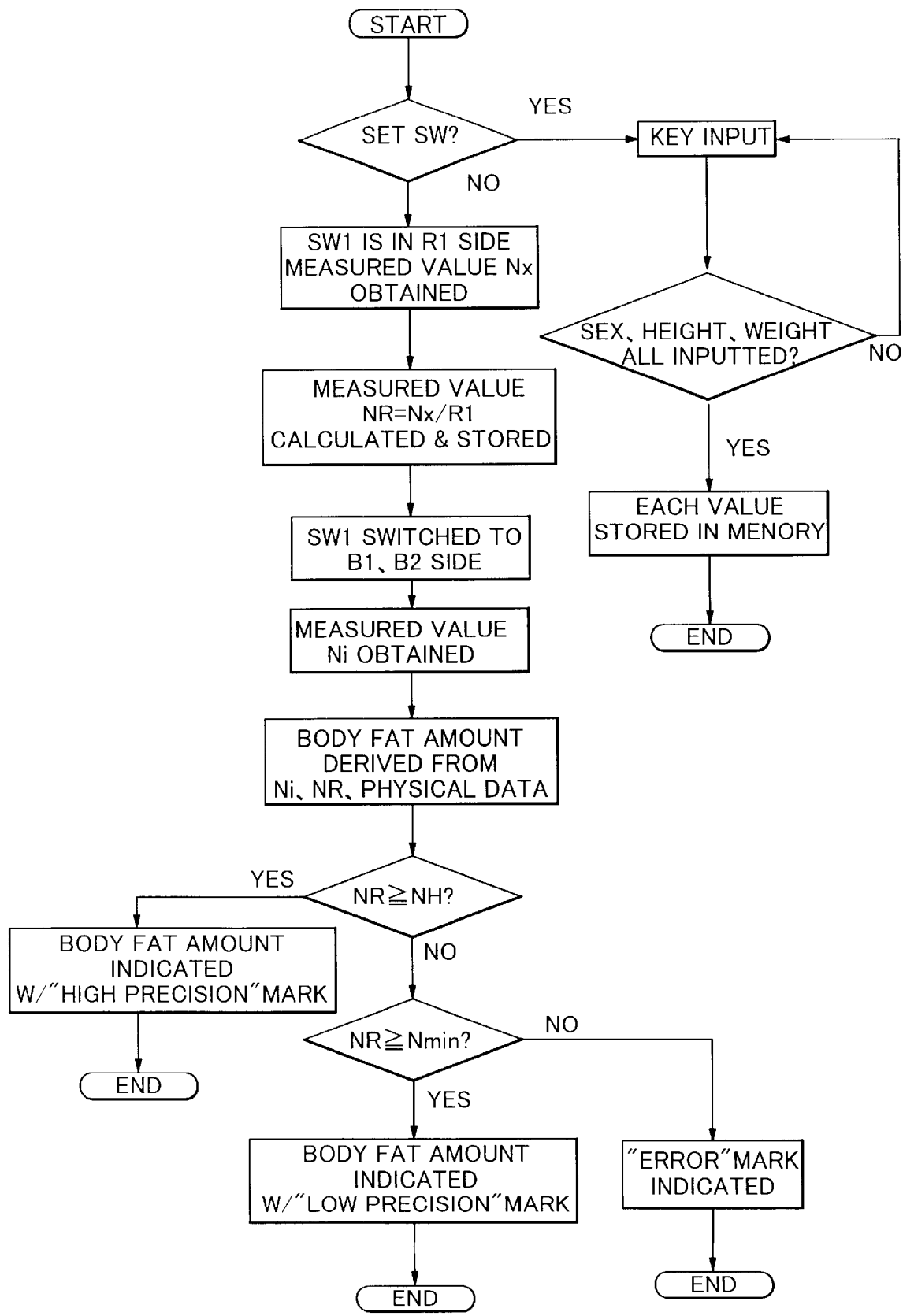
FIG. 9 is an operation flow chart of the embodiment of the present invention.

Referring now to FIGS. 6 and 7, an end of AC ammeter is connected to an AC power source of 50 kHz and another end thereof is connected to an A1 terminal. An A2 terminal is connected to the GND.

Measurement terminals of an AC voltmeter are connected to electrodes B1 and B2.

An alternation switch SW1 which selectively connects either both ends of a resistor R1 or the B1 and the B2 terminals to a differential amplifier is provided and a control terminal of the alternation switch SW1 is connected to a controller.

A voltage vx is applied by the AC voltage power source, and a current flows into A1 through a resistor R1.

An internal influent current ix is represented using a resistance rx between A1 and A2 terminals as below.

$$ix=vx/(R1+rx) \tag{14}$$

The controller connects both ends of the resistor R1 to the differential amplifier by the alternation switch SW1 and converts an output thereof into a DC voltage by a half-wave rectifier and a low pass filter, and inputs it into an A/D converter to convert it into a digital value and then stores said digital value Nx in a memory.

Thus, the voltage generated between both ends of the resistor R1 has been obtained as a digital value Nx.

Since the voltage vR1 generated between both ends of the resistor R1 is:

$$vR1=ix \times R1$$

the internal influent current ix is represented as below.

$$ix=vR1/R1$$

Since the voltage vR1 is represented by the digital value Nx and the resistance R1 is a known value, the internal influent current ix can be calculated.

Thus, a digital value NR which represents the internal influent current is calculated by the following equation:

$$NR=Nx/R1$$

and is stored in the memory.

Then, the controller connects the B1 and the B2 terminals to the differential amplifier by the alternation switch SW1 and, in the same manner, converts an output thereof into a digital value by inputting it into the A/D converter through the half-wave rectifier and the low pass filter, and then stores said digital value Ni in the memory.

Thus, the voltage vi generated by the bioelectrical impedance ri has been obtained as a digital value Ni.

Since ri=Vi/ix, the bioelectrical impedance can be found using the digital values Ni and NR.

An arithmetic processor calculates the body fat amount based on the obtained bioelectrical impedance value and the physical data of the measured person, and outputs the result into an indicator.

The embodiment described above shows an example which employs the AC ammeter using the resistor R1, and this method is very useful to the present invention.

When the AC ammeter with low voltage drop is employed, the voltage applied to the A1 terminal is nearly equal to the output vx of the AC voltage power source.

Since the internal influent current is inversely proportional to a contact impedance and an internal impedance, so that the internal influent current is increased too much when the contact impedance is extremely small. It is absolutely necessary that this current is within the range where the human body is never influenced by that.

A protective function such as that of breaker is required in which, for example, the current more than 2 mA is prevented from being applied to the AC voltage power source when the maximum allowable internal influent current is 2 mA.

When the maximum voltage of the AC voltage power source is assumed to be 2 V and the resistance R1 is to be 1 kΩ in the above embodiment, the internal influent current ix is:

$$ix=vx/(R1+rx)=2V/(1k\Omega+rx)<2 \text{ mA}$$

so that it is always less than 2 mA.

That is, the resistor R1 serves also as a unit having a function to control a current value by selecting the resistance value thereof.

When the internal influent current is too small, the precision level may be lowered sometimes. The indicator is quipped with a "high precision" mark and a "low precision" mark, and, when a digital value which represent a lower limit of current for ensuring a high precision is specified to be NH and another digital value which represent a current level less than a measurable limit is specified to be NMIN, the body fat amount is calculated and then:

the body fat amount is indicated with the light of "high precision" mark on if the digital value NR of the calculated current is as:

$$NR \geq NH,$$

the body fat amount is indicated with the light of "low precision" mark on if the digital value NR of the calculated current is represented as:

$$NH>NR>NMIN,$$

and "Error" is lighted on if the digital value NR of the calculated current is as below.

$$NR \leq NMIN$$

Thereby, even if the precision varies, the result can be easily indicated to avoid possible misunderstanding.

Though the description of the weighing instrument is omitted for simplicity in the above example, the weighing instrument can share these devices with the impedance measuring system and make it more convenient with low cost by disposing an alternation switch between the impedance measuring device and said A/D converter, connecting another end of the alternation switch to an analogue output of a weight measuring device, and connecting a control terminal of the alternation switch to said controller, so that, at first, an output of the weight measuring device is inputted into the A/D converter through the alternation switch to convert a weight value of the measured person into a digital value and store it to the memory, and then the alternation switch is switched so as for the output of the impedance measuring device to be inputted into the A/D converter.

The technology for measuring the body fat ratio more accurately without any error has been described, and, according to this, even if the socks or stockings being put on, it can be measured accurately without any error.

What is claimed is:

1. A body fat meter comprising:
   an input unit;
   an impedance measuring unit;
   an arithmetic processing unit; and
   an indicating unit;
   wherein said input unit measures or inputs at least a height as physical data of a measured person; said impedance measuring unit measures a bioelectrical impedance of the measured person; said arithmetic processing unit calculates a body fat amount by arithmetically processing the inputted physical data, a measured or inputted weight value, and the bioelectrical impedance obtained by the impedance measuring unit; and said indicating unit indicates a body fat amount calculated by the arithmetic processing unit;
   wherein said impedance measuring unit comprises:
      a constant voltage power source for supplying a predetermined constant voltage;
      a pair of voltage supply terminals for applying the predetermined voltage to a human body;
      an internal influent current measuring unit;
      an internal voltage measuring unit; and
      a calculating unit;
      wherein said internal influent current measuring unit for measuring an influent current flowing into the human body is installed between said constant voltage power source and the human body; said internal voltage measuring unit measures voltage generated by the current flowing into the human body; and said calculating unit calculates the bioelectrical impedance from the current flowing into the human body measured by said internal influent current measuring unit and the internal voltage measured by the internal voltage measuring unit.

2. A weighing instrument with body fat meter, comprising:
   an input unit;
   an impedance measuring unit;
   a weighing unit;
   an arithmetic processing unit; and
   an indicating unit;
   wherein said input unit inputs at least a height as physical data of a measured person; said impedance measuring unit measures a bioelectrical impedance of the measured person; said weighing unit measures a weight of the measured person; said arithmetic processing unit calculates a body fat amount by arithmetically processing the inputted physical data, the measured weight value, and the bioelectrical impedance obtained by the impedance measuring unit; and said indicating unit indicates a body fat amount calculated by the arithmetic processing unit;
   wherein said impedance measuring unit comprises:
      a constant voltage power source for supplying a predetermined constant voltage;
      a pair of voltage supply terminals for applying the predetermined voltage to a human body;
      an internal influent current measuring unit;
      an internal voltage measuring unit; and
      a calculating unit;
      wherein said internal influent current measuring unit for measuring an influent current flowing into the human body is installed between said constant voltage power source and the human body; said internal voltage measuring unit measures voltage generated by the current flowing into the human body; and said calculating unit calculates the bioelectrical impedance from the current flowing into the human body measured by said internal influent current measuring unit, and the internal voltage measured by the internal voltage measuring unit.

3. A body fat meter claimed in either of claims 1 or 2, in which said internal influent current measuring unit comprises a resistor disposed between the constant voltage power source and the human body, and a voltage measuring unit of said resistor.

4. A body fat meter claimed in claim 3, in which the resistor disposed between the constant voltage power source and the human body serves as a limiting resistor of the influent current for limiting the internal influent current below a predetermined value.

5. A weighing instrument with body fat meter comprising:
   an input unit;
   a weighing unit;
   an impedance measuring unit;
   an arithmetic processing unit; and
   an indicating unit;
   wherein said input unit inputs at least a sex, a height, and an age as physical data of a measured person; said weighing unit measures a weight of the measured person; said impedance measuring unit measures a bioelectrical impedance between both feet of the measured person, said impedance measuring unit having two pairs of electrodes in positions which are capable of coming in contact with soles of both feet of the measured person when said measured person gets on a loading board of said weighing unit; said arithmetic processing unit calculates a body fat amount by arithmetically processing the inputted physical data, the measured weight value, and the impedance value between both feet; and said indicating unit indicates a measured weight and a calculated body fat amount;
   wherein said impedance measuring unit comprises:

a constant voltage power source for supplying a predetermined constant voltage;

a pair of voltage supply terminals for applying the predetermined voltage to a human body;

an internal influent current measuring unit;

an internal voltage measuring unit; and a calculating unit;

wherein said internal influent current measuring unit for measuring current flowing into the human body is installed between said constant voltage power source and the human body; said internal voltage measuring unit measures voltage generated by the current flowing into the human body; and said calculating unit calculates the bioelectrical impedance from the current flowing into the human body measured by said internal influent current measuring unit, and the internal voltage measured by the internal voltage measuring unit.

6. A body fat meter as claimed in claim 1 or 2 or 5, in which said indicating unit includes a displaying unit, and said displaying unit is for displaying a degree of accuracy of measurement according to the magnitude of the measured internal influent current by one of a "high precision" mark, a "low precision" mark and a "Error" mark;

wherein said "high precision" mark is displayed together with said calculated body fat amount if the measured internal influent current (NR) is equal to or larger than a lower limit (NH) of current for ensuring a high precision such that $NR \geq NH$, said "low precision" mark is displayed together with said calculated body fat amount if the measured internal influent current NR is smaller than the lower limit of current for ensuring a high precision and larger than a measurable limit (NMIN) such that $NH > NR > NMIN$, and said "Error" mark is displayed if the measured internal influent current NR is equal to or smaller than the measurable limit NMIN such that $NR \leq NMIN$.

* * * * *